United States Patent [19]

Urabe et al.

[11] Patent Number: 5,206,272
[45] Date of Patent: Apr. 27, 1993

[54] IMPRESSION MATERIAL COMPOSITIONS

[75] Inventors: Sunao Urabe; Shouichi Narui, both of Tokuyama, Japan

[73] Assignee: Tokuyama Soda Kabushiki Kaisha, Tokuyama, Japan

[21] Appl. No.: 717,009

[22] Filed: Jun. 18, 1991

[30] Foreign Application Priority Data

Jun. 18, 1990 [JP] Japan .................................. 2-157659

[51] Int. Cl.$^5$ ............................ A61K 6/10; C08L 5/04
[52] U.S. Cl. ..................................... 523/109; 524/28; 106/35
[58] Field of Search .......................... 523/109; 524/28; 106/35

[56] References Cited

U.S. PATENT DOCUMENTS

| | | |
|---|---|---|
| 2,249,694 | 7/1941 | Wilding . |
| 2,397,145 | 3/1946 | VanBeuren Joy et al. . |
| 2,454,709 | 11/1948 | Molnar et al. . |
| 2,568,752 | 9/1951 | Lochridge . |
| 2,824,811 | 2/1958 | Erickson et al. . |
| 2,878,129 | 3/1959 | Rabchuk . |
| 3,620,778 | 11/1971 | Morrell ............................... 523/109 |
| 4,768,951 | 9/1988 | Abiru et al. ............................ 433/48 |

Primary Examiner—Joseph L. Schofer
Assistant Examiner—Jeffrey T. Smith
Attorney, Agent, or Firm—Sherman and Shalloway

[57] ABSTRACT

This invention relates to an impression material composition comprising an alginate and a gelling agent and being hardened in the presence of water, an unsaturated carboxylic acid polymer being contained in an amount of 5 to 150 parts by weight per 100 parts by weight of the alginate.

23 Claims, No Drawings

IMPRESSION MATERIAL COMPOSITIONS

This invention relates to a novel impression material composition. More specifically, this invention relates to an impression material composition comprising an alginate and a gelling agent and being hardened in the presence of water, an unsaturated carboxylic acid polymer being contained in an amount of 5 to 150 parts by weight per 100 parts by weight of the alginate.

BACKGROUND OF THE INVENTION

Impression material compositions comprising alginates and divalent or polyvalent metal salts such as calcium sulfate, zinc oxide, etc. have been known to be used in taking impression as alginate impression materials. These alginate impression materials have advantages that they are good in precision of impression, can reproduce fine parts and are easy of impressing operation; accordingly, they have been widely used as e.g. impression material compositions for dental use. In general, impression material compositions in two forms of a powder and a paste, containing inorganic fillers, are used as required In the impression material compositions in both forms, the alginate and the gelling agent are reacted in the presence of water and gelled to form an elastic hardened product. In order to obtain precise impression, it is necessary that they are kneaded sufficiently and uniformly and incorporation of air is minimized. To this end, it is advisable that viscosity of a paste in kneading the impression material composition is as low as possible. When the kneaded paste is put on a tray and pressed against a final mold, more than fixed viscosity is needed. Otherwise, the paste is poured down, the tray can hardly be kept in a given position and a gap is formed between the mold and the impression material, making it difficult to provide precise impression. Moreover, a step of kneading the impression material composition with water to form a paste and a step of taking impression are usually finished only within several minutes. In practical use, the above opposite properties are required to be imparted to one impression material composition.

The conventional impression material compositions hardly meet all of the above required properties, and they are actually used by sacrificing either viscosity for the paste or viscosity in taking impression.

SUMMARY OF THE INVENTION

It is an object of this invention to provide an impression material composition whose viscosity is low during kneading with water but is increased rapidly after kneading and reaches viscosity desirable for taking impression by pressing against a model.

Another object of this invention is to provide an impression material composition whose viscosity can be adjusted, as required, in kneading with water and in taking impression.

Still another object of this invention is to provide an impression material composition which is easy to conduct operation of taking impression.

The other objects of this invention will be clarified from the following detailed description of the invention.

DETAILED DESCRIPTION OF THE INVENTION

This invention is to provide an impression material composition comprising an alginate and a gelling agent and being hardened in the presence of water, an unsaturated carboxylic acid polymer being contained in an amount of 5 to 150 parts by weight per 100 parts by weight of the alginate.

Moreover, this invention is to provide, upon hardening in the presence of water, an impression material composition having a gelling time of 45 seconds to 4 minutes, permanent deformation of 4% or less and viscosity which is raised at two stages after the start of kneading.

The alginate used in this invention is not particularly limited, and any alginates known as a starting material of an alginate impression material are available. Examples of the alginates which are used especially preferably include sodium alginate, potassium alginate, ammonium alginate and triethanolamine alginate.

The proportion of the alginate may be selected from the known range depending on properties of the impression material required. In general, such embodiment is widely used that 2 to 10% by weight of the alginate is contained in the kneaded impression material.

The gelling agent used in this invention is not particularly limited, and any gelling agents known to be used in the alginate impression material are available. A desirable gelling agent is a divalent or polyvalent metal compound. One type of the gelling agent may be used, but from the aspects of adjustment of a gelling time and ease of operation, a combination of two or more gelling agents is employed in many cases. The most typical example of such combination is a combination of calcium sulfate and an oxide or a hydroxide of a divalent or polyvalent metal. Concrete examples of the gelling agent available in this invention include calcium sulfates such as calcium sulfate dihydrate, calcium sulfate hemihydrate and anhydrous calcium sulfate; and oxides or hydroxides of divalent or polyvalent metals such as calcium, magnesium, zinc, aluminum, iron, titanium, zirconium and tin. Examples of the oxides or the hydroxides that are most preferably used include calcium hydroxide, magnesium oxide, zinc oxide, zinc hydroxide, aluminum oxide, aluminum hydroxide, iron oxide, iron hydroxide, titanium oxide, nickel oxide, strontium oxide, strontium hydroxide, zirconium oxide and tin oxide.

Of these metal compounds, zinc oxide is most preferable because it is easily reacted with an unsaturated carboxylic acid polymer. This zinc oxide is not particularly limited, and any zinc oxides can be used. However, zinc oxide called active zinc flower having high surface reactivity is more preferable.

As the amount of the gelling agent in this invention, an amount of the gelling agent in the known alginate impression material is used as such. The amount of the gelling agent which is used most widely is 30 to 500 parts by weight per 100 parts by weight of the alginate. When using a combination of two or more gelling agents, e.g. a combination of said calcium sulfate and one or more divalent or polyvalent metal oxides or hydroxides, the amount of said calcium sulfate may be selected from the range of 30 to 500 parts by weight, and said divalent or polyvalent metal oxides or hydroxides from the range of 3 to 100 parts by weight, respectively.

The maximum feature of this invention is that 5 to 150 parts by weight, per 100 parts by weight of the alginate, of the unsaturated carboxylic acid polymer is blended as a component of the impression material composition. The impression material composition of this invention contains the alginate and the specific amount of the unsaturated carboxylic acid polymer as components that are hardened with the gelling agent. Accordingly, when the impression material composition is gelled in the presence of water, increase in viscosity is achieved at two stages. Namely, after the kneading is over, at the first stage, principally the unsaturated carboxylic acid polymer is crosslinked by the action of the gelling agent to increase viscosity, which becomes higher than viscosity in kneading. Later, when a fixed time lapses, at the second stage, principally the alginate is crosslinked by the action of the gelling agent. Thus, viscosity is rapidly raised and an elastic hardened product is finally provided.

As a result, in kneading, viscosity is so low that the uniform kneading is possible and incorporation of air can be minimized. After the kneading is finished, viscosity is raised through increase in viscosity at the first stage and reaches such viscosity that the paste is not poured down from the tray and no gap is provided between the form and the impression material; the impression material can be pressed against the form. After pressing it against the model, the elastic hardened product is given by increase in viscosity at the second stage. Thus, the impressing operation of taking impression is very easy and precise impression is enabled.

The unsaturated carboxylic acid polymer used in this invention is not particularly limited. A water-soluble polymer selected from known unsaturated carboxylic acid polymers or their salts can be used. Preferable examples thereof include homopolymers of unsaturated carboxylic acids such as acrylic acid, methacrylic acid, itaconic acid, maleic acid, glutaconic acid, aconitic acid, citraconic acid, mesaconic acid, tiglic acid, fumaric acid, allylmalonic acid, crotonic acid and vinyl acetate; copolymers of these unsaturated carboxylic acids; and their sodium salts, potassium salts, lithium salts and ammonium salts.

The unsatuated carboxylic acid polymer may be any polymer that can be crosslinked with the gelling agent. For example, a copolymer of the unsaturated carboxylic acid and another copolymerizable ethylenically unsaturated compound is preferably used. In the copolymer, the amount of the unsaturated carboxylic acid is generally selected from the range of at least 10 mol %, preferably 30 to 100 mol %. The ethylenically unsaturated compound is not particularly limited and any known compounds copolymerizable with the unsaturated carboxylic acid are available. Preferable examples of the ethylenically unsaturated compound include methyl (meth)acrylate, ethyl (meth)acrylate, 2-hydroxyethyl (meth)acrylate, n-propyl (meth)acrylate, isopropyl (meth)acrylate, phenyl (meth)acrylate, benzyl (meth)acrylate, 2-ethylhexyl (meth)acrylate, n-butyl (meth)acrylate, iso-butyl (meth)acrylate, decyl (meth)acrylate, lauryl (meth)acrylate, stearyl (meth)acrylate, 2-hydroxylpropyl (meth)acrylate, glyceryl,(meth)acrylate, 3-chloro-2-hydroxypropyl (meth)acrylate, 2,3-dibromopropyl (meth)acrylate, trimethylolethane (meth)acrylate, (meth)acrylamide, N,N-dimethyl (meth)acrylamide, vinyl acetate, styrene, alpha-methylstyrene, 2,2-bis[(meth)acryloyloxypolyethoxyphenyl)propane, 2,2'-bis[4-(3-methacryloyloxy-2-hydroxypropoxy)phenyl]-propane, (meth)acrylonitrile, acrolein, and their substituted compounds or derivatives.

As the unsaturated carboxylic acid polymer used in this invention, a homopolymer of acrylic acid or methacrylic acid and a copolymer of each of these monomers and another unsaturated carboxylic acid or ethylenically unsaturated compound are most widely used. In the above copolymer, the amount of acrylic acid or methacrylic acid as a monomer is most preferably 5 to 95 mol %.

The unsaturated carboxylic acid polymer used in this invention may be any polymer having a low to high molecular weight. In general, the weight average molecular weight may be selected from the range of 1,000 to 500,000.

The amount of the unsaturated carboxylic acid polymer used in this invention is preferably 5 to 150 parts by weight, most preferably 10 to 70 parts by weight per 100 parts by weight of the alginate. When the amount of the unsaturated carboxylic acid is less than 5 parts by weight, increase in viscosity after kneading is not enough, with the result that the impression material is poured down from the tray, the operation of taking impression is difficult and precise impression is not taken. Meanwhile, when it is larger than 150 parts by weight, viscosity is increased drastically and greatly, so that kneading of the impression material becomes insufficient and no uniform kneaded product is obtained. Further, as viscosity of the kneaded product is high, the impression material does not go into fine parts, making it impossible to provide precise impression. Moreover, when the impression material is hardened, internal stress remains. Consequently, deformation occurs when the impression material is removed and thus precise impression cannot be obtained.

The impression material composition of this invention may contain, besides the aforesaid essential components, oxides or hydroxides of metals typified by aluminum, silicon, etc. as a filler and viscous mineral materials, unless impairing the objects of this invention. Examples of the filler include diatomaceous earth, talc, silica and aluminum hydroxide. Moreover, to retard gelling of the impression material composition, phosphates such as sodium phosphate, oxalic acid and its sodium, potassium and ammonium salts may be added. Further, fluorine compounds such as sodium silicofluoride and potassium titanium fluoride may be added.

The above-described impression material composition of this invention may take a form of a powder or a paste. When using it in the form of the powder, all of the components are blended as a powder, mixed with water when used and kneaded in the form of a paste. In the impression material composition used in the form of the paste, the alginate and the unsaturated carboxylic acid polymer are mixed with water to form the paste which is mixed with the gelling agent when used. On this occasion, the gelling agent may be added in the form of the powder or in the form of the paste kneaded with a nonaqueous solvent. Examples of the non-aqueous solvent include hydrocarbons, aliphatic alcohols, cyclic alcohols, aliphatic acids, their salts or esters, polyethylene glycol and polypropylene glycol.

When the impression material composition of this invention is, as stated above, gelled by mixing it with water, crosslinking of the unsaturated carboxylic acid polymer and crosslinking of the alginate occur separately. As a consequence, said composition has low viscosity in kneading and is easy to knead. With the lapse of time, it comes to have viscosity which makes it easy to take impression. After a given period of time, viscosity is further raised, and an elastic hardened product is finally provided. Preferable results can be expected by clearly adjusting a phenomenon of achieving the above increase in viscosity at two stages. To this end, a method is also effective in which a combination of retarders is used in the two crosslinking reactions and one of them has a higher retarding effect to one reaction. For instance, a method of adding two crosslink retarding agents, i.e. a crosslink regarding agent to retard the reaction of the unsaturated carboxylic acid polymer, such as sodium pyrophosphate and a crosslink regarding agent to retard the reaction of the alginate, such as trisodium phosphate.

The impression material in this invention has a gelling time of 45 seconds to 4 minutes, permanent deformation of 4% or less of the elastic hardened product and strain in compression of 8 to 15%. Moreover, in the impression material composition, increase in viscosity is achieved at two stages after kneading. For example, it is possible to adjust viscosity such that after 15 seconds from the start of kneading, it is 1,000 poises or less and after 40 seconds from the start of kneading, it is within the range of 1,100 to 2,000 poises. Besides, the kneading time can be determined on the basis of the fact that after 30 seconds from the start of kneading, viscosity is 1,000 poises or less and after 80 seconds from the start of kneading, viscosity is within the range of 1,100 to 2,000 poises.

The impression material composition in this invention is such that by conducting the crosslinking reaction at the two stages, viscosity which is so low as to allow easy kneading is raised to viscosity necessary for taking impression immediately after kneading, and gelation occurs rapidly with the lapse of a fixed time after pressing against a model from which impression is to be taken, making it possible to provide an elastic hardened product and take precise impression.

The impression material composition in this invention can be used in taking impression for various purposes For example, it can be used in taking impression of a form of teeth or gingiva in treating the teeth, in taking impression of a model being cast when producing a mold for metal casting and in taking impression of a model being shaped in molding plastics.

The following Examples and Comparative Examples illustrate this invention more specifically. However, this invention is not limited thereto.

EXAMPLES 1 to 4

Powder components were mixed according to the formulation shown in Table 1 to prepare a powdery impression material composition. To 100 parts by weight of the powdery composition was added water in an amount shown in Table 1. The mixture was kneaded with rubber balls for 10 seconds to form a paste. Viscosity after 30 seconds and 80 seconds from the start of kneading, a gelation time, strain in compression and permanent deformation were measured. Viscosity of the paste was measured at 23° C. using a high-shear rheometer of Ishida Giken K.K. The gelling time, strain in compression and permanent deformation were measured in accordance with JIS T-6505. The results are shown in Table 1. After 30 seconds from the start of kneading, the viscosity was low, and after 80 seconds from the start of kneading, viscosity became higher and reached 1,100 to 1,400 poises. Said viscosity was most suited for taking impression. Finally, gelation occurred in a time shown in Table 1, and an elastic hardened product was formed.

COMPARATIVE EXAMPLES 1-5

For comparison, an impression material composition was prepared according to the formulation shown in Table 1, and tested as in Example 1. The results are shown in Table 2.

TABLE 1

|  |  | Example | | | |
|---|---|---|---|---|---|
|  |  | 1 | 2 | 3 | 4 |
| Sodium alginate | (parts by weight) | 12 | 12 | 12 | 12 |
| Sodium polyacrylate (average molecular weight 300,000) | (parts by weight) | 5 | 1 | 15 | 5 |
| Calcium sulfate dihydrate | (parts by weight) | 12 | 15 | 5 | 40 |
| Sodium pyrophosphate | (parts by weight) | 2 | 0.5 | 4 | 4 |
| Trisodium phosphate | (parts by weight) | 0.5 | 0.5 | 0.2 | 1.5 |
| Potassium titanium flouride | (parts by weight) | 1 | 0.5 | 1 | 2 |
| Zinc oxide (active zinc flower) | (parts by weight) | 2 | 0.5 | 10 | 3 |
| Diatomaceous earth | (parts by weight) | 65.5 | 70 | 52.8 | 32.5 |
| Amount of water in kneading | (ml) | 350 | 300 | 400 | 350 |
| Viscosity after 30 seconds | (poises) | 800 | 1000 | 500 | 850 |
| Viscosity after 80 seconds | (poises) | 1100 | 1200 | 1200 | 1200 |
| Gelling time (minutes) |  | 2.5 | 2 | 3 | 3 |
| Strain in compression (%) |  | 12 | 13 | 16 | 9 |
| Permanent deformation (%) |  | 3.0 | 3.0 | 4.0 | 3.2 |

TABLE 2

|  |  | Comparative Example | | | | |
|---|---|---|---|---|---|---|
|  |  | 1 | 2 | 3 | 4 | 5 |
| Sodium alginate | (parts by weight) | 12 | 12 | 12 | 12 | 12 |
| Sodium polyacrylate (average molecular weight 300,000) | (parts by weight) | — | 0.5 | 25 | 5 | 5 |
| Calcium sulfate dihydrate | (parts by weight) | 12 | 12 | 12 | 12 | 12 |
| Sodium pyrophosphate | (parts by weight) | 2 | 1 | 3 | 0.2 | 4 |
| Trisodium phosphate | (parts by weight) | — | 0.5 | 0.5 | 0.5 | 0.5 |
| Potassium titanium fluoride | (parts by weight) | 1 | 0.5 | 1 | 1 | 1 |
| Zinc oxide | (parts by weight) | 2 | 2 | 2 | 0.2 | 15 |

TABLE 2-continued

|  |  | Comparative Example | | | | |
|---|---|---|---|---|---|---|
|  |  | 1 | 2 | 3 | 4 | 5 |
| (active zinc flower) |  |  |  |  |  |  |
| Diatomaceous earth | (parts by weight) | 71 | 71.5 | 45.5 | 69.1 | 50.5 |
| Amount of water in kneading | (ml) | 250 | 300 | 500 | 350 | 350 |
| Viscosity after 30 seconds | (poises) | 1200 | 900 | 1300 (unkneadable) | 800 | 1250 (unkneadable) |
| Viscosity after 80 seconds | (poises) | 1200 | 950 | 1300 | 850 | 1300 |
| Gelling time (minutes) |  | 2 | 2 | 2 | 2 | 2.5 |
| Strain in compression (%) |  | 13 | 14 | unkneadable | 13 | 16 |
| Permanent deformation (%) |  | 3.0 | 3.0 | unkneadable | 3.0 | 3.8 |

EXAMPLES 5-9

Example 1 was repeated except using polyacrylic acid with different degrees of polymerization and changing its amount. The results are shown in Table 3.

EXAMPLES 10-17

Example 1 was repeated except using polymers shown in Table 1 instead of polyacrylic acid. The results are shown in Table 4.

TABLE 3

|  |  | Example | | | | |
|---|---|---|---|---|---|---|
|  |  | 5 | 6 | 7 | 8 | 9 |
| Polyacrylic acid Molecular weight |  | 1,500 | 10,000 | 150,000 | 200,000 | 450,000 |
| Amount |  | 15 | 8 | 5 | 2 | 1 |
| Viscosity after 30 seconds | (poises) | 900 | 850 | 850 | 850 | 900 |
| Viscosity after 80 seconds | (poises) | 1,150 | 1,100 | 1,150 | 1,200 | 1,200 |
| Gelling time (min.) |  | 2 | 2 | 2.5 | 2.5 | 3 |
| Strain in compression (%) |  | 12 | 12 | 12 | 12 | 12 |
| Permanent deformation (%) |  | 3.2 | 3.1 | 3.0 | 3.0 | 3.0 |

TABLE 4

|  |  | Example | | | |
|---|---|---|---|---|---|
|  |  | 10 | 11 | 12 | 13 |
| Polymer |  | Polymethacrylic acid | Acrylic acid/ methacrylic acid (1:1) copolymer | Acrylic acid/ maleic acid (1:1) co-polymer | Acrylic acid/ itaconic acid (1:1) co-polymer |
| Viscosity after 30 seconds | (poises) | 850 | 850 | 850 | 850 |
| Viscosity after 80 seconds | (poises) | 1250 | 1200 | 1150 | 1100 |
| Gelling time (minutes) |  | 2.5 | 2.5 | 2.5 | 2.5 |
| Strain in compression (%) |  | 12 | 12 | 12 | 12 |
| Permanent deformation (%) |  | 3.0 | 3.0 | 3.0 | 3.0 |

|  |  | Example | | | |
|---|---|---|---|---|---|
|  |  | 14 | 15 | 16 | 17 |
| Polymer |  | Acrylic acid/ methyl meth-acrylate (1:1) copolymer | Acrylic acid/ 2-hydroxyethyl (meth)acrylate (1:1)copolymer | Maleic acid/ isopropyl methacrylate (1:1)copolymer | Itaconic acid/ ethyl metha-crylate (1:1) copolymer |
| Viscosity after 30 seconds | (poises) | 850 | 850 | 850 | 850 |
| Viscosity after 80 seconds | (poises) | 1200 | 1200 | 1180 | 1150 |
| Gelling time (minutes) |  | 2.5 | 2.5 | 2.5 | 2.5 |
| Strain in compression (%) |  | 12 | 12 | 12 | 12 |
| Permanent deformation (%) |  | 3.0 | 3.0 | 3.0 | 3.0 |

EXAMPLES 18-19

Example 1 was repeated except using metallic compounds shown in Table 5 instead of zinc oxide. The results are shown in Table 5.

TABLE 5

|  | Example 18 | Example 19 |
|---|---|---|
| Metal oxide or hydroxide | Magnesium oxide | Aluminum hydroxide |
| Viscosity after 30 seconds (poises) | 950 | 950 |
| Viscosity after 80 seconds (poises) | 1150 | 1100 |
| Gelling time (min.) | 2.5 | 2.5 |
| Strain in compression | 12 | 12 |
| Permanent deformation | 3.0 | 3.2 |

EXAMPLE 20

Ten grams of a paste comprising 12 parts by weight of sodium alginate, 5 parts by weight of sodium polyacrylate and 220 parts by weight of water was mixed with 1 g of a powder comprising 15 parts by weight of sodium sulfate dihydrate, 2 parts by weight of sodium pyrophosphate, 0.5 part by weight of trisodium phosphate and 3 parts by weight of zinc oxide to form an impression material. Evaluation was conducted as in Example 1. After 30 minutes from the start of kneading, viscosity was 70 poises, and after 80 minutes from the start of kneading, it was 1,150 poises. Three minutes later, gelation occured, and a hardened product was obtained having strain in compression of 12% and permanent deformation of 3.0%.

EXAMPLES 21-24

Components were mixed in accordance with the formulation shown in Table 6 to prepare an impression material composition comprising pastes A and B. These pastes A and B were kneaded at a ratio of 5:1, and evaluation was conducted as in Example 1. The results are shown in Table 6. After 30 seconds from the start of kneading, viscosity was low. After 80 seconds from the start of kneading, viscosity became higher and reached 1,100 to 1,400 poises, which was most suitable for taking impression. Finally, gelation occured in a time shown in Table 6, and an elastic hardened product was provided.

kneading, it became 1,100 poises. Three minutes later, gelation occurred and a hardened product was obtained having strain in compression of 12% and permanent deformation of 2.0%.

EXAMPLES 26-29

Powdery components were mixed in accordance with the formulation shown in Table 7 to prepare a powdery impression material. To 100 parts by weight of the powdery composition was added water in an amount shown in Table 7. The mixture was kneaded with rubber balls for 10 seconds to form a paste. Viscosity after 15 seconds and 40 seconds from the start of kneading, a gelation time, strain in compression and permanent deformation were measured as in Example 1. The results are shown in Table 7. After 15 seconds from the start of kneading, viscosity was low, and after 40 seconds from the start of kneading, viscosity became

TABLE 6

|  |  |  | Example 21 | Example 22 | Example 23 | Example 24 |
|---|---|---|---|---|---|---|
| Paste A | Sodium alginate | (parts by weight) | 12 | 12 | 12 | 12 |
|  | Unsaturated carboxylic acid polymer (avagerge molecular weight 200,000) | (parts by weight) | Sodium polyacrylate 7 | Acrylic acid/ itaconic acid (1:1)copolymer 5 | Acrylic acid/ methyl methacrylate (1:1) copolymer 10 | Methacrylic acid/methyl methacrylate (1:1)copolymer 5 |
|  | Water | (parts by weight) | 220 | 220 | 220 | 210 |
| Paste B | Calcium sulfate hemihydrate | (parts by weight) | 15 | 15 | 15 | 15 |
|  | Sodium pyrophosphate | (parts by weight) | 2 | 2 | 2 | 2 |
|  | Trisodium phosphate | (parts by weight) | 0.5 | 0.5 | 0.7 | 0.4 |
|  | Zinc oxide | (parts by weight) | 5 | 5 | 8 | 4 |
|  | Flowable paraffin | (parts by weight) | 7 | 7 | 9 | 6 |
| Viscosity after 30 seconds |  | (poises) | 500 | 700 | 800 | 800 |
| Viscosity after 80 seconds |  | (poises) | 1100 | 1200 | 1400 | 1200 |
| Gelling time (min.) |  |  | 3 | 3 | 3 | 3 |
| Strain in compression |  |  | 12 | 12 | 12 | 12 |
| Permanent deformation |  |  | 2.0 | 2.0 | 2.2 | 2.3 |

EXAMPLE 25

Ten grams of a paste A comprising 12 parts by weight of sodium alginate, 7 parts by weight of sodium polyacrylate and 220 parts by weight of water and 2 g of a paste B comprising 15 parts by weight of calcium sulfate hemihydrate, 2 parts by weight of sodium pyrophosphate, 0.5 part by weight of trisodium phosphate, 5 parts by weight of zinc oxide and 7 parts by weight of a flowable paraffin were mixed to form an impression material. Evaluation was conducted as in Example 1. After 30 seconds from the start of kneading, viscosity was 500 poises, and after 80 seconds from the start of high and reached 1,100 to 1,400 poises, which was most suitable for impression. Finally, gelation occured in a time shown in Table 7, and an elastic hardened product was provided.

TABLE 7

|  |  | 26 | 27 | 28 | 29 |
|---|---|---|---|---|---|
| Sodium alginate | (parts by weight) | 12 | 12 | 12 | 12 |
| Sodium polyacrylate (average molecular weight 300,000) | (parts by weight) | 5 | 1 | 15 | 5 |
| Calcium sulfate dihydrate | (parts by weight) | 12 | 15 | 5 | 40 |
| Sodium pyrophosphate | (parts by weight) | 1 | 0.2 | 1 | 2 |
| Trisodium phosphate | (parts by weight) | 0.2 | 0.2 | 0.2 | 0.5 |
| Potassium titanium fluoride | (parts by weight) | 1 | 0.5 | 1 | 2 |
| Zinc oxide (acitve zinc flower) | (parts by weight) | 2 | 0.5 | 10 | 3 |
| Diatomaceous earth |  | 65.5 | 70 | 52.8 | 32.5 |
| Amount of water in kneading |  | 350 | 300 | 400 | 350 |
| Viscosity after 15 seconds | (poises) | 800 | 1000 | 500 | 850 |
| Viscosity after 40 seconds | (poises) | 1100 | 1200 | 1300 | 1200 |
| Gelling time (min.) |  | 1 | 1 | 1 | 1 |
| Strain in compression (%) |  | 12 | 13 | 16 | 9 |
| Permanent deformation (%) |  | 3.0 | 3.0 | 4.0 | 3.2 |

What is claimed is:

1. An impression material composition comprising:
   (A) 100 parts by weight of a water soluble alginate salt,
   (B) 5 to 100 parts by weight of an unsaturated carboxylic acid polymer or its water-soluble salt,
   (C) 30 to 500 parts by weight of anhydrous or hydrated calcium sulfate, and (D) 3 to 100 parts by weight of an oxide or hydroxide of a divalent or polyvalent metal which is capable of converting the unsaturated carboxylic acid polymer (B) into its insoluble form, through its reaction with the unsaturated carboxylic acid polymer;

said composition being characterized in that, it is easily kneaded with water, and after kneading with water the viscosity of the kneaded material increases in two stages, in which (1) in the first stage a gel of a water-insoluble, unsaturated carboxylic acid polymer is formed by reaction of above component (B) with the component (D), and thereafter, (2) in the second stage a hardened product of a water-insoluble alginate is formed by reaction of above component (A) with the component (C).

2. An impression material composition as defined in claim 1, in which, when water is added to the composition comprising the components (A), (B), (C) and (D) and kneaded together, (1) due to the reaction of the component (B) with the component (D) in the first stage, at 30 seconds after start of the kneading, the viscosity of the impression material composition increases to up to 1000 poises, and (2) due to the reaction of the component (A) with the component (C) in the second stage, at 80 seconds after start of the kneading, the viscosity of the impression material composition increases to within the range of 1,100 to 2,000 poises.

3. The impression material composition of claim 1 wherein the alginate is an alkali metal or amine salt of alginic acid.

4. The impression material composition of claim 1 wherein the gelling agent is at least one polyvalent metal oxide or hydroxide.

5. The impression material of claim 1 which further comprises (E) a crosslinking retarding agent effective to retard the first stage reaction and (F) a crosslinking retarding agent effective to retard the second stage reaction.

6. The impression material composition of claim 1 wherein the unsaturated carboxylic acid polymer is an unsaturated carboxylic acid homopolymer.

7. The impression material composition of claim 6 wherein the unsaturated carboxylic acid polymer is an acrylic or methacrylic acid homopolymer.

8. The impression material composition of claim 1 wherein the unsaturated carboxylic acid polymer is a copolymer of the unsaturated carboxylic acid and another unsaturated carboxylic acid.

9. The impression material composition of claim 8 wherein the unsaturated carboxylic acid polymer is a copolymer of acrylic acid or methacrylic acid and maleic acid or itaconic acid.

10. The impression material composition of claim 1 wherein the unsaturated carboxylic acid polymer is a copolymer of the unsaturated carboxylic acid and another copolymerizable ethylenically unsaturated compound.

11. The impression material composition of claim 1 wherein the alginate (A), the unsaturated carboxylic acid polymer (B) and the gelling agents (C) and (D) are stored in one container in the form of a powder mixture and mixed with water when used.

12. The impression material composition of claim 1 in the form of a two part paste composition wherein the alginate (A) and the unsaturated carboxylic acid polymer (B) are mixed with water and stored in one container in the form of a paste, the gelling agents (C) and (D) are stored in another container in the form of a paste, and both the pastes are mixed when used.

13. An impression material composition comprising
(A) 100 parts by weight of a water soluble alginate salt,
(B) 5 to 100 parts by weight of an unsaturated carboxylic acid polymer or its water-soluble salt,
(C) 30 to 50 parts by weight of anhydrous or hydrated calcium sulfate, and
(D) 3 to 100 parts by weight of zinc oxide; said composition being characterized in that, it is easily kneaded with water, and after kneading with water the viscosity of the kneaded material increases in two stages, in which (1) in the first stage a gel of a water-insoluble, unsaturated carboxylic acid polymer is formed by reaction of above component (B) with the component (D), and thereafter, (2) in the second stage a hardened product of a water-insoluble alginate is formed by reaction of above component (A) with the component (C).

14. An impression material composition as defined in claim 13, in which, when water is added to the composition comprising the components (A), (B), (C) and (D) and kneaded together, (1) due to the reaction of the component (B) with the component (D) in the first stage, at 30 seconds after start of the kneading, the viscosity of the impression material composition increases to up to 1000 poises, and (2) due to the reaction of the component (A) with the component (C) in the second stage, at 80 seconds after start of the kneading, the viscosity of the impression material composition increases to within the range of 1,100 to 2,000 poises.

15. The impression material of claim 1 having a setting time of from 45 seconds to 4 minutes and a permanent deformation of 4% or less and strain in compression of 8 to 15%.

16. The impression material of claim 15 wherein the alginate is present in an amount of from 2 to 10% by weight of the impression material.

17. The impression material of claim 1 wherein the unsaturated carboxylic acid polymer contains from 30 to 100 mol % of units derived from an unsaturated carboxylic acid.

18. The impression material of claim 17 wherein the amount of the unsaturated carboxylic acid polymer (B) is 10 to 70 parts by weight.

19. The impression material of claim 5 which comprises sodium pyrophosphate as crosslinking retarding agent (E) and trisodium phosphate as crosslinking retarding agent (F).

20. The impression material of claim 15 wherein component (D) is zinc oxide.

21. The impression material of claim 17 wherein component (D) is zinc oxide.

22. The impression material of claim 18 wherein component (D) is zinc oxide.

23. The impression material of claim 5 wherein component (D) is zinc oxide.

* * * * *